(12) United States Patent
Qin et al.

(10) Patent No.: US 9,125,851 B2
(45) Date of Patent: Sep. 8, 2015

(54) ACTIVE SMALL-MOLECULE DONKEY-HIDE GELATIN MIXTURE AND PREPARATION METHOD AND APPLICATION THEREOF

(71) Applicant: SHANDONG DONG-E E-JIAO CO., LTD., Liaocheng, Shandong province (CN)

(72) Inventors: Yufeng Qin, Liaocheng (CN); Jinhua You, Liaocheng (CN); Xiangshan Zhou, Liaocheng (CN); Zhe Fang, Liaocheng (CN)

(73) Assignee: SHANGDONG DONG-E E-JIAO CO., LTD., Liaocheng (CN)

( * ) Notice: Subject to any disclaimer, the term of this patent is extended or adjusted under 35 U.S.C. 154(b) by 0 days.

(21) Appl. No.: 14/353,536

(22) PCT Filed: Nov. 21, 2012

(86) PCT No.: PCT/CN2012/001566
§ 371 (c)(1),
(2) Date: Apr. 23, 2014

(87) PCT Pub. No.: WO2013/097274
PCT Pub. Date: Jul. 4, 2013

(65) Prior Publication Data
US 2014/0315819 A1    Oct. 23, 2014

(30) Foreign Application Priority Data
Dec. 29, 2011 (CN) .......................... 2011 1 0450564

(51) Int. Cl.
| | |
|---|---|
| *A61K 38/01* | (2006.01) |
| *A23L 1/305* | (2006.01) |
| *C07K 14/78* | (2006.01) |
| *A61K 35/36* | (2015.01) |

(52) U.S. Cl.
CPC ............. *A61K 38/014* (2013.01); *A23L 1/3053* (2013.01); *A61K 35/36* (2013.01); *C07K 14/78* (2013.01)

(58) Field of Classification Search
CPC .... A23L 1/3053; C07K 14/78; A61K 38/014; A61K 35/36
See application file for complete search history.

(56) References Cited

U.S. PATENT DOCUMENTS

2011/0165306 A1* 7/2011 Dekker et al. ................. 426/590

FOREIGN PATENT DOCUMENTS

| CN | 101019890 A | * 8/2007 | ............ A61K 35/36 |
|---|---|---|---|
| CN | 101285087 | 10/2008 | |
| CN | 102321716 | 1/2012 | |

OTHER PUBLICATIONS

Machine translation of CN 101285087 A, pp. 1-22, accessed Jul. 30, 2014.*
Machine translation of CN 102321716 A, pp. 1-14, accessed Mar. 17, 2015.*
Machine translation of CN 101019890 A, pp. 1-8, accessed Mar. 17, 2015.*
Silk, Peptide absorption in man, Gut, 1974, 15, pp. 494-501.*
English translation of Tables 1 and 2 of CN 102321716 A, p. 1, accessed Mar. 24, 2015.*
International Search Report filed in PCT/CN2012/001566 mailed Feb. 28, 2013.

* cited by examiner

*Primary Examiner* — Julie Ha
*Assistant Examiner* — Li Ni Komatsu
(74) *Attorney, Agent, or Firm* — Rankin, Hill & Clark LLP

(57) ABSTRACT

An active small-molecule donkey-hide gelatin mixture and a preparation method and application thereof. The active small-molecule donkey-hide gelatin mixture is prepared by using the compound protease comprising the proline protease to perform the enzymatic hydrolysis on the donkey-hide gelatin juice to which no auxiliary material is added. For the active small-molecule donkey-hide gelatin mixture, the weight-average molecular weight ranges from 580 Da to 1300 Da, the peptide segments are distributed from 200 Da to 3000 Da, the dissolution rate in cold water is high, and the content of free amino acid is low; the active small-molecule donkey-hide gelatin mixture may be used for manufacturing small-molecule peptide food and health care food of donkey-hide gelatin.

14 Claims, 2 Drawing Sheets

Figure 1:
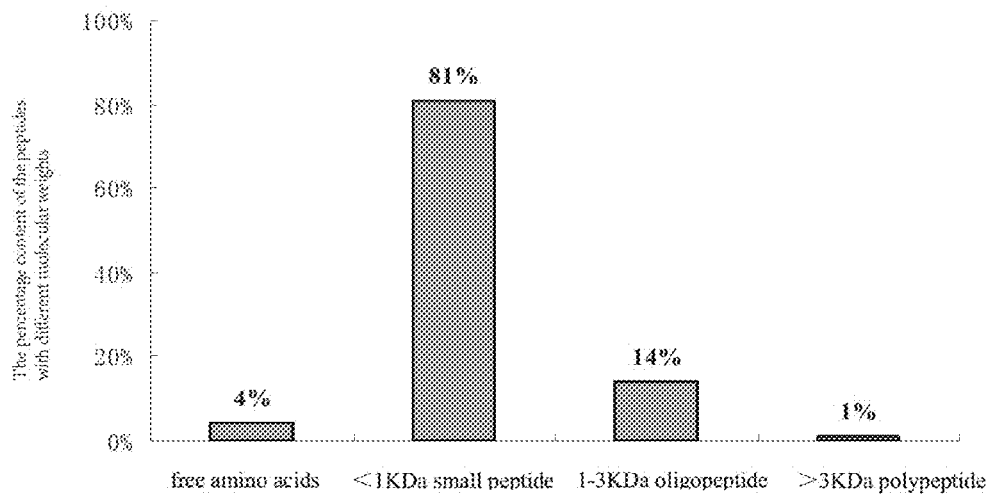

ACTIVE SMALL-MOLECULE DONKEY-HIDE GELATIN MIXTURE AND PREPARATION METHOD AND APPLICATION THEREOF

CROSS-REFERENCE TO RELATED APPLICATIONS

This application is a national stage application of international application PCT/CN2012/001566 filed Nov. 21, 2012, which claims priority to Chinese patent application CN201110450564.1 filed on Dec. 29, 2011, both of which are incorporated herein by reference in their entirety.

FIELD OF THE TECHNIQUE

This invention refers to an active small-molecule mixture and preparation method and application thereof, in particular, refers to an active small-molecule peptides mixture by enzymatic hydrolysis on donkey-hide gelatin juice, as well as the application method and application thereof. This invention belongs to the field of food biotechnology.

BACKGROUND

Donkey-hide gelatin (E-jiao) is an effective medicine for replenishing blood and nourishing Qi. In as early as the Eastern Han Dynasty, it had listed as "top grade medicine" in the famous medicine book "Shen Nong's Herbal Classic", and it was documented that "taking permanently, it can replenish Qi and cause a feeling of body weight reduction". The characteristic of Donkey-hide gelatin is Gan, mild-natured, its main function is to replenish blood and nourish Yin, to moisturize dryness, and stop bleeding. It is used for treating blood deficiency chlorosis, dizziness, palpitation, muscle atrophy and weakness, irritability, insomnia, internal agitation of deficient Wind, cough owing to dryness in the lung and over-strain, chatter of blood, vomiting blood and hematuria, stool bleeding, threatened abortion and so on. According to the 2010 edition of Chinese Pharmacopoeia, Donkey-hide gelatin is a solid gelatin produced by boiling the dried or fresh skin of equidae donkey and then concentrating the decoction. However, the molecular weights of collagen proteins are too large (from tens of thousands to hundreds of thousands) to be absorbed by patients with weak spleen and stomach, which result in inadequate performance of functions of Donkey-hide gelatin. Meanwhile, the breeding stocks of donkeys have been declining in recent years, this directly results in inadequate supply of donkey skin, and the rising price of Donkey-hide gelatin. The growing deficiency in the supply of donkey skin material cannot meet the requirements of the market, whereas because of the small-molecule Donkey-hide gelatin by enzymatic hydrolysis on donkey-hide gelatin juice can significantly increase the bioavailability of Donkey-hide gelatin, it can be a good measure to solve the contradiction between supply and demand.

In recent years, researches on enzymolysis of Donkey-hide gelatin have made some progresses, a number of patents have been published, including: (1) "A method for the preparation of liquid Donkey-hide gelatin by enzymolysis", Publication No. is CN1237421A; (2) "Active Donkey-hide gelatin collagen peptide products", Publication No. is CN1807653A; (3) "A preparation method for Donkey-hide gelatin hydrolyzate with low molecular weight", Publication No. is CN101269090A. These three inventions all reported the production of collagen peptides by means of protease digestion of Donkey-hide gelatin. Based on the existing technology, this invention takes advantage of characteristically high proline and hydroxyproline contents in Donkey-hide gelatin, proposes to enzymatically digest it by using proline protease for the first time, results in significantly better hydrolysis than that had been reported in the previous patents. In the above-mentioned 3 patents, most of the molecular weights of the products were distributed in the range of less than 5000 Da, even less than 10000 Da. Besides, none of the patents reported the accurate measurement of molecular weight distribution and the free amino acid contents, whereas in the present invention, the peptide molecular weight is distributed in the range of 200-3000 Da, mainly in 200-1000 Da; in patents CN1237421A and CN1807653A, both of them used the Donkey-hide gelatin lumps with auxiliary material added as the digestion raw material, whereas in the present invention, Donkey-hide gelatin juice is used as the raw material for enzymolysis in order to simplify the process, save cost, and result in products with good solubility and high bioavailability, the clearance rate of DPPH and ABTS radicals are close to 100%.

Many reports in the literature (Adibi A S. America Nutrition, 1984, 25: 1114-1122; DBA Silk Gut, 1974, 15: 494-501) stated that peptides with the molecular weights in the range of 200-1000 Da demonstrated superior absorption and efficacy in comparison with peptides of other size and free amino acids. The present invention proposes to use Donkey-hide gelatin juice without auxiliary material as raw materials, to accurately determine the free amino acid contents in the products and the molecular weight distribution of the products, and the small peptides contained in the products distribute mostly in the range of 200-1000 Da, therefore their absorption and efficacy are better.

SUMMARY OF THE INVENTION

To solve the problems in the existing technique, one of the objects of the present invention is to provide an active small-molecule donkey-hide gelatin mixture.

The second object of the present invention is to provide a method for the production of the active small-molecule donkey-hide gelatin mixture.

The third object of the present invention is to provide the application of said active small-molecule donkey-hide gelatin mixture in the production of small-molecule-peptide foods and health foods.

To attain the above objects, the present invention adopts the following technical means:

An active small-molecule donkey-hide gelatin mixture proposed in the present invention, wherein the weight-average molecular weight of the product is 580-1300 Da, peptides distribute between 200-3000 Da, mainly between 200-1000 Da.

In the present invention, an active small-molecule donkey-hide gelatin mixture is prepared by using compound protease to perform the enzymatic hydrolysis on donkey-hide gelatin juice. Said compound proteases comprise papain and proline protease, preferably, said compound proteinase further includes one or several or all protease selected from the group consisting of bromelain protease, neutral protease, pepsin and flavourzyme.

In the present invention, said active small-molecule donkey-hide gelatin mixture can be processed into powdered or liquid formulation.

Features of the active small-molecule donkey-hide gelatin mixture proposed in the present invention are: (1) it can be processed into a powdered or a liquid formulation for oral administration; (2) it has good solubility and a high dissolution rate even in cold water; (3) it has low contents of free amino acids (only 4%), small peptides with molecular weight in the range of 200-1000 Da account for 81% of the total, those in the range of 1000-3000 Da account for 14% (See FIG. 1), the weight-average molecular weight is 765 Da; (4) with respect to bioavailability, that of small molecule donkey-hide gelatin is 3.5 times that of ordinary donkey-hide gelatin, is 2.2 times that of the bionically digested donkey-hide gelatin (See FIG. 2); (5) in terms of antioxidant efficacy, small molecule donkey-hide gelatin shows a good efficacy of scavenging radicals including DPPH and ABTS, at a concentration of 10 mg/ml, the clearance rates can be nearly 100% (see FIGS. 3 and 4).

The present invention also provides a method to produce the active small-molecule donkey-hide gelatin mixture, wherein the following procedures are comprised:

(1) Cool the auxiliary material-free donkey-hide gelatin juice down to 30-55° C. at room temperature, adjust the pH to 5-8, add in compound proteases into the juice to bring about hydrolysis reaction for 0.5 to 2 hours, thereby obtaining the hydrolyzate of donkey-hide gelatin juice;

(2) Maintain boiling the hydrolyzate of donkey-hide gelatin juice obtained in step (1) for 10-30 minutes to inactivate the enzyme, thereby obtaining the inactivated decoction;

(3) Centrifuge the inactivated decoction to remove impurities, thereby obtaining the liquid formulation of the active small-molecule donkey-hide gelatin mixture.

The method to prepare said the active small-molecule donkey-hide gelatin mixture proposed in the present invention may further comprise spray drying said liquid formulation to produce powdered formulation of the active small-molecule donkey-hide gelatin mixture.

In the method proposed in this invention, said auxiliary material include yellow rice wine, crystal sugar and soybean oil; said auxiliary material-free donkey-hide gelatin juice is the donkey-hide gelatin juice to which no yellow rice wine, crystal sugar or soybean oil added.

In embodiments of this invention, the concentration of the donkey-hide gelatin juice in step (1) is 10%~50% (w/w).

In embodiments of the invention, said compound proteases comprise papain and proline protease, preferably, said compound proteinase further includes one or several or all protease selected from the group consisting of bromelain protease, neutral protease, pepsin and flavourzyme.

In embodiments of the present invention, wherein the amount of the compound proteases added in step (1) is 5%0-3% weight (w/w) of the donkey-hide gelatin juice, the order of addition of the compound proteases is: these enzymes added chronologically at regular intervals, or these enzymes added simultaneously in the initial stages of the hydrolysis reaction.

In a particular embodiment of the present invention, according to the weight, the addition ratio of each of the compound protease is: papain:proline protease=2:1; or papain:proline proteases:any one of bromelain, neutral protease, pepsin or flavourzymes=5:2:1. Other ratios will not be expatiated. The person in the art may make wide varieties of choices based on the actual situation in the application without any creative work.

The present invention further provides the application of the active small-molecule donkey-hide gelatin mixture in the preparation of small-molecule-peptide foods and health foods. The small molecule active peptide mixture results in better absorption, shows very good solubility and very good antioxidant effect, so it favors the development of foods of powdered or liquid formulation, as well as health foods with antioxidant and aging-delaying functions.

Compared to the existing technique, the advantages of the present invention are:

1, the proposed method utilizes donkey-hide gelatin juice without any auxiliary material as raw material, thereby realizing simplification of the process, energy conservation, cost lowering, high efficiency of hydrolysis, and assurance of the stability of the structure and properties of the spray-drying product.

2, the proposed method eliminates fat and impurities in the product by centrifugation, to ensure that the solubility of the product is high, and that it is conducive to the development of related foods and health foods.

3, in the proposed method, a powdered raw material is obtained by using spray-drying, to ensure a low storage cost, and easy development of capsule and granule products.

4, in the proposed method, the test technique of the product is advanced, to ensure accurate determination of contents of the free amino acids and distribution of peptides.

5, in the proposed method, enzymolytic technology is advanced, molecular weight of the peptides in the product are mainly distributed between 200-1000 Da, this molecular weight range is lower than those obtained by published processes, thereby ensuring better absorption and functional effects.

6, the production technology proposed in this invention is advanced and practical, ensuring a high yield of small molecule mixture from donkey-hide gelatin. For example, using 1 L 40% donkey-hide gelatin juice as raw material, after enzymolysis and subsequent process, the obtained powdery product was about 360 g, with a yield of 90%.

7, preliminary determination of bioavailability and antioxidant efficacy of the material obtained showed very good results.

BRIEF DESCRIPTION TO THE ACCOMPANYING DIAGRAMS

FIG. 1: Molecular weight distribution of an active small-molecule donkey-hide gelatin mixture determined using high performance gel chromatography in combination with amino acid analysis technique.

Figure 2:
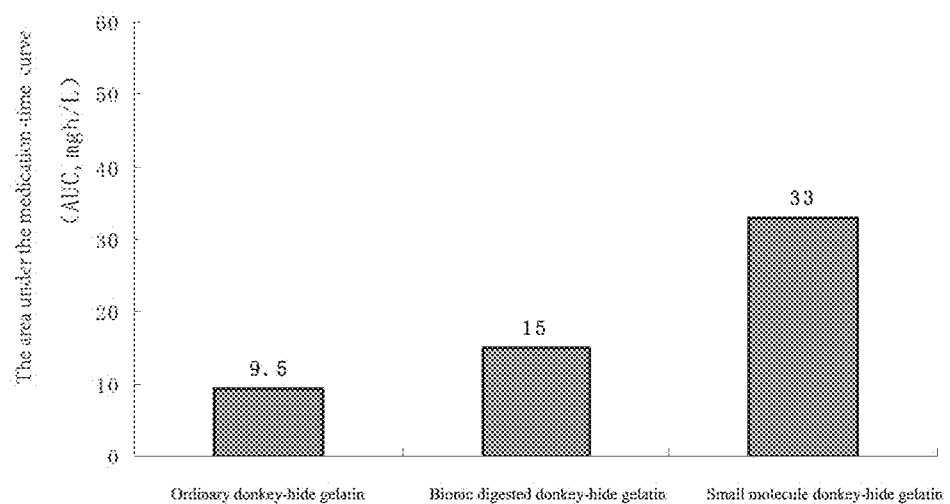
Figure 3:
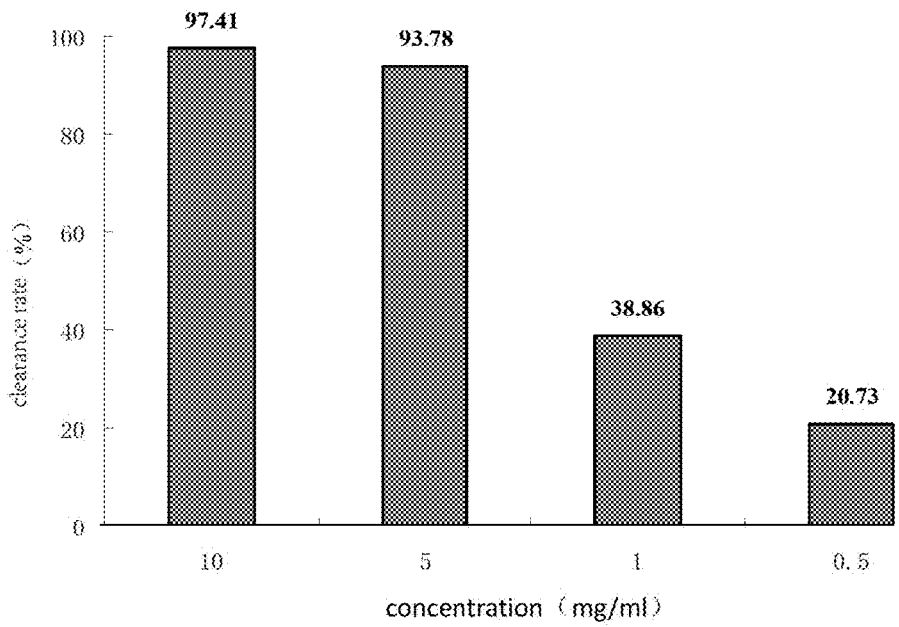
Figure 4:
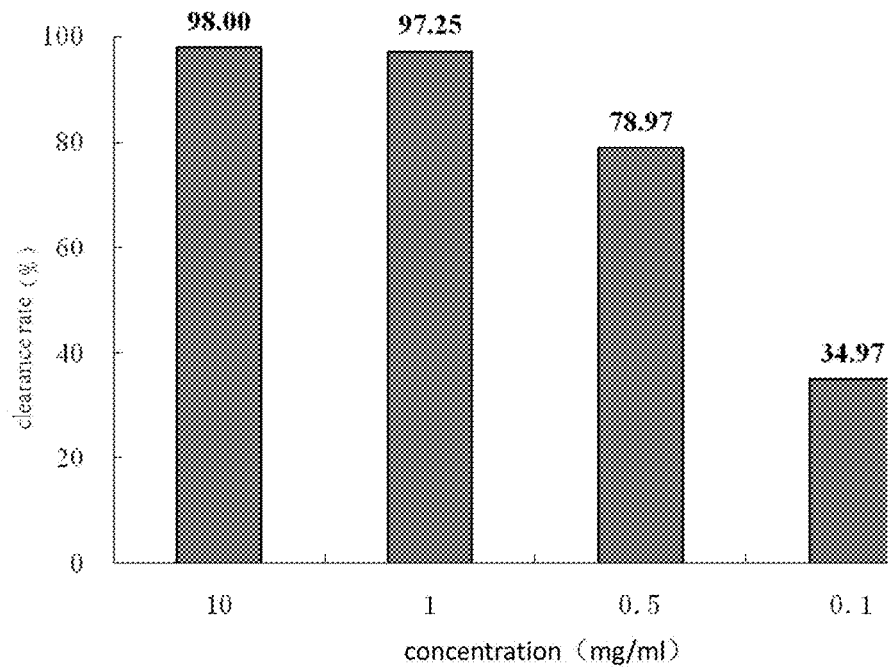

FIG. 2: A comparison of the bioavailability by comparing hydroxyl proline contents in the blood of mice after feeding with the product according to the invention as well as those according to different techniques; wherein, Ordinary donkey-hide gelatin: normal untreated donkey-hide gelatin sample;

Bionic digested donkey-hide gelatin: enzymolysis of donkey-hide gelatin using pepsin and intestinal trypsin imitating the digestion in human gastrointestinal tract;

Small molecule donkey-hide gelatin: an active small-molecule donkey-hide gelatin mixture obtained by using the method proposed in the present invention;

FIG. 3: DPPH radical scavenging effect of an active small-molecule donkey-hide gelatin mixture obtained according to the present invention;

FIG. 4: ABTS radical scavenging effect of an active small-molecule donkey-hide gelatin mixture obtained according to the present invention.

EMBODIMENTS

Following are further demonstrations of this invention with embodiments. The merit and characteristics of this invention will be made clearer by the demonstrations. It should be understood that these embodiments are only exemplary, and are by no means a restriction to the protection scope of this invention. The person in the art should appreciate that, without departing from the spirit and scope of the present invention, they can modify or replace details and form of the present invention, but all such modifications and replacements will fall within the scope of protection to the present invention.

Sources of experimental materials involved in the embodiment of the present invention:

1, Donkey-hide gelatin juice containing no yellow rice wine, crystal sugar and soybean oil was purchased from Shandong Dong-E Donkey-hide gelatin Co., Ltd.;

2, various enzymes flavourzyme, neutral protease and bromelain were purchased from Pangbo Bioengineering Co., Ltd., Nanning, China; Papain and pepsin were purchased from Keyuan Industrial Co., Ltd.; Proline protease was purchased from Shanghai Yuanda Business Ltd.;

3, ABTS and DPPH radical were purchased from Sigma Aldrich Co., Ltd.

Example 1

Cooling down 1 L of the donkey-hide gelatin juice (40% (w/w)) without addition of auxiliary materials to 35° C. at room temperature, adjusting its pH to 6.5. Adding 5% (w/w) of compound proteases (papain: proline protease=2:1 (w/w)) to the juice to bring about hydrolysis reaction for 2 hours, heating to boil the juice and maintaining boil for 20 minutes subsequently to deactivate the enzymes, followed by centrifugation to remove insoluble impurities and fat, to obtain a liquid preparation of active small-molecule donkey-hide gelatin mixture. A determination of the molecular weight of the product showed that most of the peptides were in the range of 200-3000 Da, accounting for 83% of the total.

Example 2

Cooling down 1 L of the donkey-hide gelatin juice (40% (w/w)) without addition of auxiliary materials to 35° C. at room temperature, adjusting its pH to 6.5. Adding 5% (w/w) of compound proteases (papain: proline protease=2:1 (w/w)) to the juice to bring about hydrolysis reaction for 2 hours, maintaining boil of the juice for 20 minutes subsequently to deactivate the enzymes, followed by centrifugation to remove insoluble impurities and fat, finally, spray-drying the liquid to obtain 360 g powdered active small-molecule donkey-hide gelatin mixture. A determination of the molecular weight of the product showed that most of the peptides were in the range of 200-3000 Da, accounting for 83% of the total.

Example 3

Cooling down 1 L of the donkey-hide gelatin juice (40% (w/w)) without addition of auxiliary materials to 40° C. at room temperature, adjusting its pH to 5.5. Adding 1% (w/w) of compound proteases (papain: proline protease: pepsin=5:2:1 (w/w)) to the juice to bring about hydrolysis reaction for 2 hours, maintaining boil of the juice for 20 minutes subsequently to deactivate the enzymes, followed by centrifugation to remove insoluble impurities and fat, finally, spray-drying the liquid to obtain 360 g powdered active small molecule donkey-hide gelatin mixture. A determination of the molecular weight of the product showed that most of the peptides were in the range of 200-3000 Da, accounting for 86% of the total.

Example 4

Cooling down 1 L of the Donkey-hide gelatin juice (10% (w/w)) without addition of auxiliary materials to 35° C. at room temperature, adjusting its pH to 6. Adding 2% (w/w) of compound proteases (papain:proline protease:neutral protease:pepsin:flavourzyme=6:3:1:1:1 (w/w)) to the juice to bring about hydrolysis reaction for 2 hours, maintaining boil of the juice for 20 minutes subsequently to deactivate the enzymes, followed by centrifugation to remove insoluble impurities and fat, finally, spray-drying the liquid to obtain 360 g powdered active small-molecule donkey-hide gelatin mixture. A determination of the molecular weight of the product showed that most of the peptides were in the range of 200-3000 Da, accounting for 75% of the total.

Example 5

Cooling down 1 L of the donkey-hide gelatin juice (40% (w/w)) without addition of auxiliary materials to 50° C. at room temperature, adjusting its pH to 6.5. Adding 3% (w/w) of compound proteases (papain:proline protease:pepsin:neutral protease:flavourzyme=6:2:2:1:1 (w/w)) to the juice to bring about hydrolysis reaction for 2 hours, maintaining boil of the juice for 20 minutes subsequently to deactivate the enzymes, followed by centrifugation to remove insoluble impurities and fat, finally, spray-drying the liquid to obtain 360 g powdered active small-molecule donkey-hide gelatin mixture. A determination of the molecular weight of the product showed that most of the peptides were in the range of 200-3000 Da, accounting for 95% of the total.

Example 6

Cooling down 1 L of the donkey-hide gelatin juice (40% (w/w)) without addition of auxiliary materials to 40° C. at room temperature, adjusting its pH to 6.5. Adding 3% (w/w) of compound proteases (papain:proline protease:pepsin:neutral protease:flavourzyme=6:2:2:1:1 (w/w)) to the juice to bring about hydrolysis reaction for 0.5 hours, heating to boil the juice and maintaining boil for 20 minutes subsequently to deactivate the enzymes, followed by centrifugation to remove insoluble impurities and fat, finally, spray-drying the liquid to obtain 360 g powdered active small-molecule donkey-hide gelatin mixture. A determination of the molecular weight of the product showed that most of the peptides were in the range of 200-3000 Da, accounting for 83% of the total.

Example 7

Cooling down 1 L of the donkey-hide gelatin juice (40% (w/w)) without addition of auxiliary materials to 40° C. at room temperature, adjusting its pH to 6.5. Adding 5% (w/w) of compound proteases (papain:proline protease:pepsin:neutral protease:flavourzyme=6:2:2:1:1 (w/w)) to the juice to bring about hydrolysis reaction for 2 hours, heating to boil the juice and maintaining boil for 20 minutes subsequently to deactivate the enzymes, followed by centrifugation to remove insoluble impurities and fat, finally, spray-drying the liquid to obtain 360 g powdered active small-molecule donkey-hide gelatin mixture. A determination of the molecular weight of the product showed that most of the peptides were in the range of 200-3000 Da, accounting for 71% of the total.

Example 8

Cooling down 1 L of the donkey-hide gelatin juice (40% (w/w)) without addition of auxiliary materials to 40° C. at room temperature, adjusting its pH to 6.5. Adding 1.5% (w/w) of compound proteases (papain:proline protease=2:1 (w/w)) to the juice to bring about hydrolysis reaction for 0.5 hours, followed by addition of 5% (w/w) pepsin to continue the hydrolysis for 0.5 hours, followed by continuation of the hydrolysis by addition of 5% (w/w) compound proteases (neutral protease:flavourzyme=1:1 (w/w)) for 1 hour, heating to boil the juice and maintaining boil for 20 minutes subsequently to deactivate the enzymes, followed by centrifugation to remove insoluble impurities and fat, finally, spray-drying the liquid to obtain 360 g powdered active small molecule donkey-hide gelatin mixture. A determination of the molecular weight of the product showed that most of the peptides were in the range of 200-3000 Da, accounting for 87% of the total.

Example 9

Cooling down 1 L of the donkey-hide gelatin juice (40% (w/w)) without addition of auxiliary materials to 50° C. at room temperature, adjusting its pH to 6.5. Adding 3% (w/w) of compound proteases (papain:pepsin:neutral protease:flavourzyme:bromelain=6:2:2:1:1 (w/w)) to the juice to bring about hydrolysis reaction for 2 hours, heating to boil the juice and maintaining boil for 20 minutes subsequently to deactivate the enzymes, followed by centrifugation to remove insoluble impurities and fat, finally, spray-drying the liquid to obtain 360 g powdered active small-molecule donkey-hide gelatin mixture. A determination of the molecular weight of the product showed that most of the peptides were in the range of 200-3000 Da, accounting for 65% of the total.

The powdered active small-molecule donkey-hide gelatin mixture prepared according to Example 5 of embodiment of this invention was used in the following test analysis.

Example 10

The Test of the Distribution of the Peptides in the Active Small-Molecule Donkey-Hide Gelatin Mixture 1.1 Tests Using High Performance Gel Chromatography
Test Equipment:
Liquid System: Agilent 1100; efficient gel column: TSK-G2000 SKwl (300 mm*7.8 mm, the average pore size 500 Å).
Test Procedure:
Measuring 1 ml hydrolysis samples and centrifuging at 10,000 g for 2 minutes, filtering the supernatant through a 0.45 μm disposable filter vials and the samples being subsequently injected into the chromatograph. The column temperature was 27° C., the mobile phase was 0.05 mol/L phosphate buffer (pH 7.2) with a flow rate of 0.5 ml/min, the detection wavelength was 280 nm, and the injection volume was 20 μl.

1.2 Test for Free Amino Acid Contents
Test Equipment:
MS: 3200 Q Trap; LC system: Shimadzu UFLC system; column: AB Sceix specially for the analysis of amino acids; guard column: C18 (4.0×3.0 mm, 5 μm), Phenomenex Co.
Procedures:
Adding 5 μL precipitant into 20 μL homogeneously mixed liquid sample, blending uniformly, centrifuging for 2 minutes at 10,000 g, adding 20 μL labeling buffer into 5 μL supernatant, mixing into homogeneity, adding 5 μL supernatant with 2.5 μL labeling reagent, mixing into homogeneity, reacting at room temperature for 30 min, after the reaction, adding 2.5 μL hydroxylamine, mixing into homogeneity, blowing dry with nitrogen at 40° C., recomposing by adding 16 μL internal standard solution, mixing into homogeneity, measuring 16 μL into a sample vial, injecting 5 μL into the chromatograph to measure concentrations of amino acids.

1.3 Results
The results are shown in FIG. 1. As can be seen from FIG. 1, the sample contained a high content (81%) of peptides with molecular weights ranging from 200-1000 Da, the segment of peptide between 1000-3000 Da accounted for 14% of the total, free amino acid content was very low, only 4%. The weight average molecular weight was 765 Da. As stated in Background of this invention: peptides with molecular weights between 200-1000 Da showed better absorption and efficacy in comparison with peptides of other sizes and free amino acids, it can thus be accepted that, in comparison with other collagen peptide products, the product according to present invention is superior with respect to the absorption rate as well as functional efficacy.

Example 11

Bioavailability Test

Material:
Ordinary donkey-hide gelatin: normal untreated donkey-hide gelatin sample;
Bionic digested donkey-hide gelatin: enzymolysis of donkey-hide gelatin using pepsin and intestinal trypsin imitating the digestion in human gastrointestinal tract;
Small molecule donkey-hide gelatin: an active small-molecule donkey-hide gelatin mixture obtained by using the method proposed in the present invention;

Using 24 healthy mice, half male and half female, weighing between 200-250 g, randomly divided into groups A, B and C. Fasting for 12 h before medication. Administering intragastrically into groups A, B and C with ordinary donkey-hide gelatin solution, bionically digested donkey-hide gelatin solution and small molecule donkey-hide gelatin, respectively (1 mg samples/10 g body weight each) in the next morning, resuming feeding 4 h after administration. Collecting orbital blood samples 0 h, 0.25 h, 0.5 h, 1 h, 2 h, 3 h, 4 h, 6 h, 8 h, 10 h, 12 h, 18 h, 24 h after administration. After pretreatment analyzing the blood samples using amino acid analysis to obtain blood hydroxyl proline contents to calibrate bioavailability of the samples (hydroxyl proline is the characteristic amino acid of collagen).

The results are shown in FIG. 2, it can be seen from FIG. 2 that, bioavailability of the active small-molecule donkey-hide gelatin mixture proposed in the present invention is 3.5 times that of the ordinary donkey-hide gelatin, 2.2 times that of the product obtained from bionic digestion. These data demonstrated the active small-molecule donkey-hide gelatin mixture proposed in this invention has characteristics of small molecules and high absorption rate.

Example 12

Test on Antioxidant Effect 1.1 Investigation on the Effect of DPPH Radical Scavenging
Procedures
Adding 1.5 mL sample solution and 1.5 mL DPPH solution in a stoppered test tube, shaking and reacting in the dark for 30 min, measuring absorbance at 517 nm ($A_S$), simultaneously determining absorbance of the mixture of 1.5 mL 0.1 mmol/L DPPH solution and 1.5 mL ethanol ($A_C$), as well as that of the mixture of 1.5 mL sample solution and 1.5 mL ethanol ($A_B$). Calculate the clearance rate according to the following formula:

$$\text{Clearance rate}(\%) = 1 - \frac{A_S - A_B}{A_C} \times 100$$

Where $A_S$, $A_C$, and $A_B$ are the absorbance of the reactant between sample solution, as well as that of the mixture of DPPH solution and ethanol, and that of the mixture of sample solution and ethanol, respectively.

1.2 Investigation on the Effect of ABTS Radical Scavenging

Test Procedure

Reacting 88 µL potassium persulfate solution with 5 mL ABTS solution in the dark for 16 h, subsequently diluting the reactant with ethanol until the absorbance reaches 0.7±0.002. Reacting 200 µL (2 mL) ABTS reaction solution with 100 µL (1 mL) sample solution in a 96-well plate for 10 min, measuring the absorbance at 734 nm. Calculating the clearance rate according to the following formula:

$$\text{Clearance rate}(\%) = \frac{A_0 - A}{A_0} \times 100$$

Where $A_0$ is the absorbance of the ABTS$^{·+}$ solution, A is the absorbance of ABTS$^{·+}$ solution after adding the sample solution.

1.3 Results

The results are shown in FIG. 3 and FIG. 4. As can be seen from FIGS. 3 and 4, the small molecules of different concentrations of small-molecule donkey-hide gelatin solution all demonstrated the effect of scavenging ABTS and DPPH radicals, small-molecule donkey-hide gelatin solution of 10 mg/ml concentration showed close to 100% clearance on both radicals, indicating that the product according to the present invention has a certain effect on anti-oxidation.

The invention claimed is:

1. An active small-molecule donkey-hide gelatin mixture, wherein the weight-average molecular weight of the mixture is between 580-1300 Da, wherein 65%-95% of peptides in the mixture have molecular weights distributed between 200-3000 Da, wherein the mixture is prepared by using proteases to perform the enzymatic hydrolysis on donkey-hide gelatin juice, and the proteases include papain and proline protease.

2. The active small-molecule donkey-hide gelatin mixture according to claim 1, wherein the proteases further include one or several or all proteases selected from the group consisting of bromelain protease, neutral protease, pepsin, and flavourzyme.

3. The active small-molecule donkey-hide gelatin mixture according to claim 1, wherein the formulation of the mixture is a powder or a liquid.

4. The active small-molecule donkey-hide gelatin mixture according to claim 1, wherein 83% of the peptides in the mixture have molecular weights distributed between 200-3000 Da.

5. The active small-molecule donkey-hide gelatin mixture according to claim 4, wherein 81% of the peptides in the mixture have molecular weights distributed between 200-1000 Da.

6. The active small-molecule donkey-hide gelatin mixture according to claim 1, wherein 81% of the peptides in the mixture have molecular weights distributed between 200-1000 Da.

7. A method to produce the active small-molecule donkey-hide gelatin mixture according to claim 1, the method comprising:
   (1) cooling auxiliary material-free donkey-hide gelatin juice down to 30-55° C. at room temperature, adjusting the pH to 5-8, adding proteases into the juice to hydrolyze the juice for 0.5 to 2 hours, thereby obtaining the hydrolyzate of donkey-hide gelatin juice; wherein the proteases include papain and proline protease;
   (2) boiling the hydrolyzate of donkey-hide gelatin juice obtained in step (1) for 10-30 minutes to inactivate the proteases, thereby obtaining the inactivated decoction;
   (3) centrifuging the inactivated decoction to remove impurities, thereby obtaining the liquid formulation of the active small-molecule donkey-hide gelatin mixture.

8. The method according to claim 7, wherein the obtained liquid formulation of the active small-molecule donkey-hide gelatin mixture is further processed into a powder formulation by spray drying.

9. The method according to claim 7, wherein the auxiliary material is selected from the group consisting of yellow rice wine, crystal sugar, soybean oil, or a combination thereof.

10. The method according to claim 7, wherein the concentration of the donkey-hide gelatin juice in step (1) is 10%~50% by weight.

11. The method according to claim 7, wherein the proteases further include one or several or all protease selected from the group consisting of bromelain protease, neutral protease, pepsin and flavourzyme.

12. The method according to claim 7, wherein the amount of added proteases is 0.5%~3% by weight of donkey-hide gelatin juice, and the proteases are added in the sequence of several proteases added in chronological order at regular intervals, or several proteases added simultaneously in the initial stages of hydrolysis reaction.

13. The method according to claim 7, wherein the weight ratio of the added proteases is: papain:proline protease=2:1; or papain:proline protease:any one of bromelain, neutral protease, pepsin, or flavourzyme=5:2:1.

14. A method of preparing a small-molecule-peptide foods or health foods comprising the active small-molecule donkey-hide gelatin mixture according to claim 1, the method comprising introducing the active small-molecule donkey-hide mixture according to claim 1 into the small-molecule-peptide foods or health foods.

* * * * *